(12) United States Patent
Vaquero et al.

(10) Patent No.: US 8,535,331 B2
(45) Date of Patent: Sep. 17, 2013

(54) IOL INJECTOR

(75) Inventors: Edward Vaquero, Fairport, NY (US); Thomas M. Heyman, Placentia, CA (US)

(73) Assignee: Bausch & Lomb Incorporated, Rochester, NY (US)

( * ) Notice: Subject to any disclaimer, the term of this patent is extended or adjusted under 35 U.S.C. 154(b) by 1666 days.

(21) Appl. No.: 10/813,861

(22) Filed: Mar. 31, 2004

(65) Prior Publication Data
US 2005/0222577 A1 Oct. 6, 2005

(51) Int. Cl.
*A61F 9/00* (2006.01)
*A61F 2/16* (2006.01)

(52) U.S. Cl.
USPC .......................................... 606/107; 623/6.12

(58) Field of Classification Search
USPC ................................ 606/107; 623/6.12, 6.11
See application file for complete search history.

(56) References Cited

U.S. PATENT DOCUMENTS

| | | | |
|---|---|---|---|
| 4,573,998 A | 3/1986 | Mazzocco | |
| 4,681,102 A | 7/1987 | Bartell | |
| 4,702,244 A | 10/1987 | Mazzocco | |
| 4,706,669 A | 11/1987 | Schlegel | |
| 4,715,373 A | 12/1987 | Mazzocco et al. | |
| 4,765,329 A | 8/1988 | Cumming et al. | |
| 4,834,094 A | 5/1989 | Patton et al. | |
| 4,836,201 A | 6/1989 | Patton et al. | |
| 4,919,130 A | 4/1990 | Stoy et al. | |
| 4,926,877 A | 5/1990 | Bookwalter | |
| 4,934,363 A | 6/1990 | Smith et al. | |
| 5,123,905 A | 6/1992 | Kelman | |
| 5,190,552 A | 3/1993 | Kelman | |
| 5,275,604 A | 1/1994 | Rheinish et al. | |
| 5,304,182 A | 4/1994 | Rheinish et al. | |
| 5,312,413 A | 5/1994 | Eaton et al. | |
| 5,425,734 A | 6/1995 | Blake | |
| 5,474,562 A | 12/1995 | Orchowski et al. | |

(Continued)

FOREIGN PATENT DOCUMENTS

| | | |
|---|---|---|
| EP | 0270257 A1 | 6/1988 |
| JP | 5-103808 | 4/1993 |
| WO | WO 01/64147 A1 | 9/2001 |
| WO | WO 03/077805 A1 | 9/2003 |

OTHER PUBLICATIONS

U.S. Appl. No. 10/651,785, Vaquero et al.
U.S. Appl. No. 10/813,862, Vaquero et al.

(Continued)

*Primary Examiner* — Tuan V Nguyen
(74) *Attorney, Agent, or Firm* — Jeffrey B Powers

(57) ABSTRACT

A device for injecting an intraocular lens (IOL) into an eye, the device having an injector body including a lumen and an open tip wherethrough the IOL is expressed from the device. An IOL loading bay is located in the passageway wherein the IOL is positioned and compressed. The injector tip is dimensioned to allow the surgeon to choose an insertion depth between first, second and third transition points defined on the tip, the first and second transition points having a larger diameter than the third transition point which is located closer to the open tend of the tip. If the surgeon wishes to insert through a very small incision size (e.g., about 2.4 mm), the surgeon will insert the tip only up to the third transition point. The injector is stable during delivery of the IOL therethrough due to a spreading of the tip within the eye which effectively anchors the tip during IOL delivery.

18 Claims, 4 Drawing Sheets

(56) References Cited

U.S. PATENT DOCUMENTS

| | | | |
|---|---|---|---|
| 5,494,484 A | 2/1996 | Feingold | |
| 5,496,328 A | 3/1996 | Nakajima et al. | |
| 5,499,987 A | 3/1996 | Feingold | |
| 5,772,666 A * | 6/1998 | Feingold et al. | 606/107 |
| 5,810,834 A * | 9/1998 | Heyman | 606/107 |
| 5,876,406 A | 3/1999 | Wolf et al. | |
| 6,010,510 A * | 1/2000 | Brown et al. | 606/107 |
| 6,056,757 A * | 5/2000 | Feingold et al. | 606/107 |
| 6,387,101 B1 | 5/2002 | Butts et al. | |
| 6,447,520 B1 * | 9/2002 | Ott et al. | 606/107 |
| 6,491,697 B1 | 12/2002 | Clark et al. | |
| 2002/0022881 A1 | 2/2002 | Figueroa et al. | |
| 2002/0193805 A1 | 12/2002 | Ott et al. | |
| 2003/0216745 A1 | 11/2003 | Brady et al. | |

OTHER PUBLICATIONS

Charters, "Small incision possible with single-piece lens injector system," Cataract, (p. 47), (Mar. 15, 2003).

* cited by examiner

IOL INJECTOR

BACKGROUND OF THE INVENTION

The present invention relates to ophthalmic surgical devices and methods. More particularly, the present invention relates to a device and method for inserting an intraocular lens (IOL) into an eye.

IOLs are artificial lenses used to replace the natural crystalline lens of the eye when the natural lens has cataracts or is otherwise diseased. IOLs are also sometimes implanted into an eye to correct refractive errors of the eye in which case the natural lens may remain in the eye together with the implanted IOL. The IOL may be placed in either the posterior chamber or anterior chamber of the eye. IOLs come in a variety of configurations and materials. Some common IOL styles include the so-called open-looped haptics which include the three-piece type having an optic and two haptics attached to and extending from the optic; the one-piece type wherein the optic and haptics are integrally formed (e.g., by machining the optic and haptics together from a single block of material); and also the closed looped haptic IOLs. Yet a further style of IOL is called the plate haptic type wherein the haptics are configured as a flat plate extending from opposite sides of the optic. The IOL may be made from a variety of materials or combination of materials such as PMMA, silicone, hydrogels and silicone hydrogels, etc.

Various instruments and methods for implanting the IOL in the eye are known. In one method, the surgeon simply uses surgical forceps having opposing blades which are used to grasp the IOL and insert it through the incision into the eye. While this method is still practiced today, more and more surgeons are using more sophisticated IOL inserter devices which offer advantages such as affording the surgeon more control when inserting the IOL into the eye. IOL inserter devices have recently been developed with reduced diameter insertion tips which allow for a much smaller incision to be made in the cornea than is possible using forceps alone. Smaller incision sizes (e.g., less than about 3 mm) are preferred over larger incisions (e.g., about 3.2 to 5+mm) since smaller incisions have been attributed to reduced post-surgical healing time and complications such as induced astigmatism.

Since IOLs are very small and delicate articles of manufacture, great care must be taken in their handling. In order for the IOL to fit through the smaller incisions, they need to be folded and/or compressed prior to entering the eye wherein they will assume their original unfolded/uncompressed shape. The IOL inserter device must therefore be designed in such a way as to permit the easy passage of the IOL through the device and into the eye, yet at the same time not damage the delicate IOL in any way. Should the IOL be damaged during delivery into the eye, the surgeon will most likely need to extract the damaged IOL from the eye and replace it with a new IOL, a highly undesirable surgical outcome.

Thus, as explained above, the IOL inserter device must be designed to permit easy passage of the IOL therethrough. It is equally important that the IOL be expelled from the tip of the IOL inserter device and into the eye in a predictable orientation and manner. Should the IOL be expelled from the tip too quickly or in the wrong orientation, the surgeon must further manipulate the IOL in the eye which could result in trauma to the surrounding tissues of the eye. It is therefore highly desirable to have an inserter device which allows for precise loading of the IOL into the inserter device and which will pass and expel the IOL from the inserter device tip and into the eye in a controlled, predictable and repeatable manner.

To ensure controlled expression of the IOL through the tip of the IOL inserter device, the IOL must first be loaded into the IOL inserter device. The loading of the IOL into the inserter device is therefore a precise and very important step in the process. Incorrect loading of an IOL into the inserter device is oftentimes cited as the reason for a failed IOL delivery sequence. In a typical IOL inserter device, the IOL inserter utilizes a plunger having a tip which engages the IOL (which has been previously loaded and compressed into the inserter lumen) to pass it through the inserter lumen. The IOL thus interfaces with the plunger tip as well as the lumen of the inserter device. The lumen typically is dimensioned with a narrowing toward the open tip thereof in order to further compress the IOL as it is advanced through the lumen. The tip of the lumen is sized for insertion through the surgical incision which, as stated above, is presently preferred in the sub 3 mm range. Thus, an inserter lumen will typically be dimensioned larger at the load area of the IOL and gradually decrease in diameter to the tip of the lumen where the IOL is expressed into the eye. It will be appreciated that the compressed diameter of the IOL at the lumen tip is the same as the inner diameter of the lumen tip, preferably sub 3 mm as stated above. Each of these component interfaces are dynamic in the sense that the forces acting between the interfacing components (i.e., the IOL, the plunger tip and the inserter lumen) will vary as the IOL is pushed through the lumen. Control of these dynamic forces is therefore of utmost importance or otherwise the IOL may be damaged during delivery due to excessive compressive forces acting thereon. For example, as the IOL is advanced by the plunger through an ever-decreasing diameter lumen, the IOL is being compressed while at the same time the forces necessary to push the IOL through the lumen increase. This may lead to excessive force between the plunger tip and the IOL resulting in possible damage to the IOL and/or uncontrolled release of the IOL from the lumen tip. Also, the force of the plunger tip may cause the IOL to twist and/or turn as it is moved through the inserter whereby the force between the IOL and the plunger tip and/or the inserter lumen may uncontrollably increase to the point of IOL damage.

Various inserter devices have been proposed which attempt to address these problems, yet there remains a need for an IOL inserter and method which reliably places an IOL into an eye through a small incision and reduces the likelihood of IOL damage during delivery through the injector device.

SUMMARY OF THE INVENTION

The injector comprises a device body defining a longitudinal passageway (lumen) terminating at an open tip wherethrough the IOL is expressed from the injector into an eye. A plunger having a longitudinal plunger shaft and a plunger tip telescopes with the lumen of the device body. An opening is provided in the device body to access the lumen wherein an IOL is positioned. The injector includes means for compressing, rolling or otherwise forcing the IOL into a smaller cross-section for delivery through the injector. In one possible embodiment, the injector device includes a compressor drawer which extends laterally of the IOL loading bay of the injector body. The compressor drawer is movable between fully open and fully closed positions and is initially in the open position. Once the IOL is positioned in the opening or loading bay of the passageway, the compressor drawer is moved to the closed position which compresses the IOL. The plunger is advanced at the proximal end of the injector device causing the tip of the plunger to engage the proximal end of the compressed IOL. As the plunger is advanced further, the IOL is pushed through the open distal tip of the injector body and expressed into the eye in the intended manner.

For purposes of description, the tip may be considered as having four contiguous segments $S_1$-$S_4$ between the main body portion wherein the IOL is initially loaded into the device, and the open end of the tip. The first, proximal segment $S_1$ is closest to the main body, the fourth, distal segment $S_4$ includes the open tip, and the second and third segments $S_2$, $S_3$ extend sequentially therebetween. The first proximal segment $S_1$ tapers gradually inwardly for a first length $L_1$ to gradually further compress the IOL as it is being advanced by the plunger toward the open end of the tip. The second segment $S_2$ preferably has a substantially constant diameter for a second length $L_2$ which is preferably smaller than length $L_1$. The juncture of the first and second lengths define a first transition point $T_1$ having an outer diameter of about 2.7 mm to about 3.1 mm, and more preferably about 2.8 mm. Since the second segment $S_2$ preferably remains constant in diameter, the IOL is not compressed any further as it is passed through this segment by the plunger and will not enlarge an incision of the same size. The third segment $S_3$ tapers inwardly at a greater rate than the taper of segment $S_1$ for a length $L_3$ that is preferably smaller than $L_1$ or $L_2$. The juncture of the second and third segments $S_2$, $S_3$ define a second transition point $T_2$ having an outer diameter the same as at $T_1$. The fourth segment $S_4$ preferably has a continuous cross-section extending for a length $L_4$ also preferably smaller than $L_1$ or $L_2$, terminating in a slanted end face defining the open end of the tip. The juncture of the third and fourth segments $S_3$, $S_4$ defines a third transition point $T_3$ that has an outer diameter in the range of about 2.0 to 2.6 mm and more preferably about 2.4 mm.

Some surgeons will use the injector device by inserting the tip up to the first or second transition points $T_1$, $T_2$ which have an outer diameter not exceeding about 3.0 mm. This means the incision in the eye need not be larger than about 3 mm. Current surgeon preference is to have an incision no larger than about 3 mm, and preferably sub 3 mm. Yet there are other surgeons that may prefer an even smaller incision size on the order of about 2.4 mm. For these surgeons, they may insert the tip up to only the third transition point $T_3$ which, as stated above, has an outer diameter in the range of about 2.0 to 2.6 mm and more preferably about 2.4 mm.

At least one but preferably two slots extend from the second transition point $T_2$ to the tip open end face. The slots reduce the hoop (radial) strength of the tip along the third and fourth segments for reasons explained below. The slots may colinearly extend from respective grooves extending along the inside wall of the lumen through the tip wherein opposite sides of the IOL optic slide during passage of the IOL through the device and into the eye. Since the slots reduce the hoop strength of the tip along segments $S_3$ and $S_4$, those segments can spread outwardly under the force exerted by the compressed IOL as it travels through those segments. For surgeons who prefer to insert the tip only up to the third transition point $T_3$, the fourth segment $S_4$ will spread open within the eye as the IOL is passed therethrough. This spreading action of this portion of the tip effectively "anchors" the inserted portion (segment $S_4$) of the tip in the eye until the IOL has completely exited the device. This anchoring effect is important in preventing the surgeon from losing control of the IOL insertion process, especially in those circumstances where the surgeon prefers to insert only up to the point of the third transition point $T_3$ to maintain a very small diameter incision (i.e., in the range of about 2.0 to 2.5 mm). To explain, with only a small length of the tip inserted through the incision (i.e., up to point $T_3$), and without such anchoring of the tip within the eye, the force of the IOL exiting the tip may cause an inserter to decenter and/or kick back from the incision, possibly resulting in incorrect placement within the eye or the IOL expressing from the tip completely outside of the eye. The anchoring effect of the inventive tip thus ensures the tip will remain centered in the incision and in the eye until the IOL is completely expressed from the tip. Once the IOL is fully expressed from the tip into the eye, the resiliency of the tip causes the tip to return to its normal diameter allowing easy withdrawal from the eye with no stretching of the incision.

DETAILED DESCRIPTION

Figure 1A:
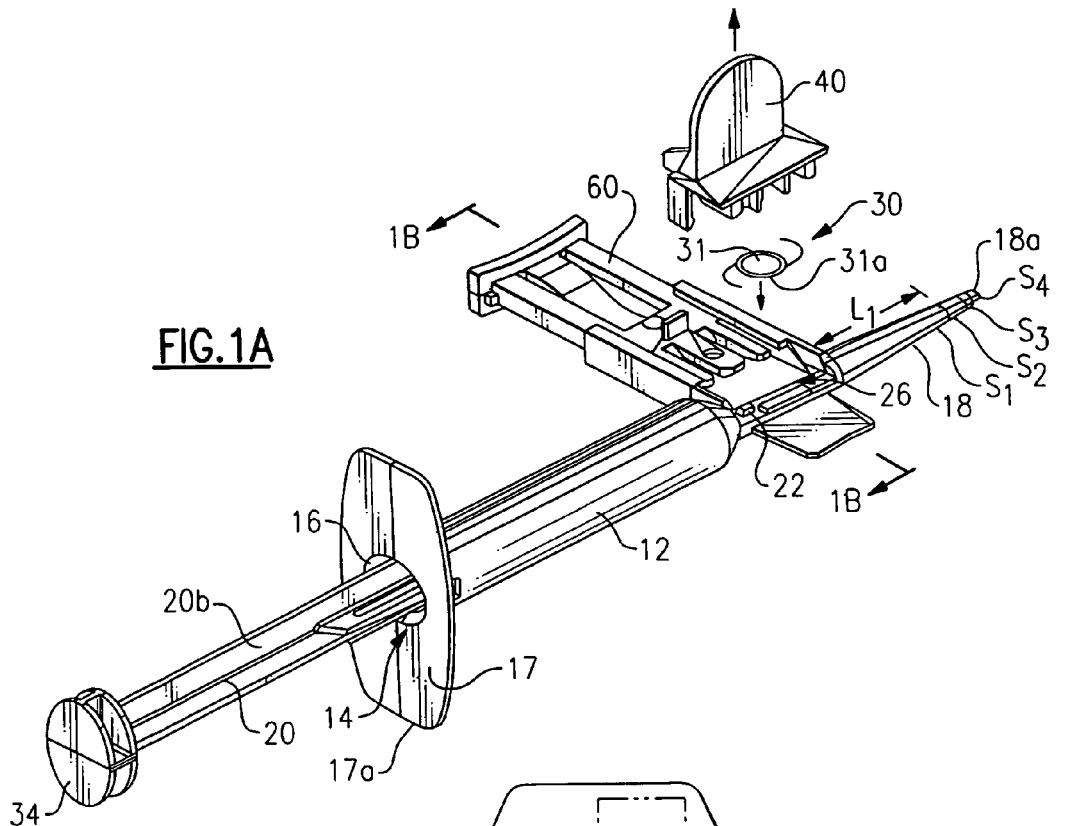
FIG. 1A is a perspective view of an exemplary IOL injector incorporating the inventive tip.

Referring to FIG. 1A, a representative IOL injector device is indicated generally by the reference numeral 10. The injector device 10 includes an injector body 12 having a longitudinal lumen 14 extending from the proximal end 16 to distal open end 18a thereof. The lumen may assume any desired cross-sectional shape although circular or oval shapes are preferred. Proximal end 16 may include a finger hold flange 17 preferably configured with a straight edge 17a as shown for resting device 10 on a flat surface. A plunger 20, having a distal plunger tip 22 and proximal thumb press 24, telescopes within lumen 14 for engaging and pushing the IOL 30 through lumen 14 and out of distal tip 18a. It is understood that the overall configuration of the injector body 12 may vary from that shown and described herein. It is furthermore understood that the components of the injector device 10 may be made of any suitable material (e.g., polypropylene) and may be wholly or partly opaque, transparent or translucent to better visualize the IOL within the injector device and the IOL delivery sequence.

Injector body 12 further includes an opening 26 which opens into lumen 14. Opening or "IOL loading bay" 26 accepts an IOL 30 therein for delivery of the IOL out distal tip 18a. In one possible embodiment, an IOL retainer 40 such as described in commonly owned copending application Ser. Nos. 10/651,785 and 10/813,862 incorporated herein by reference, is used for loading the IOL 30 into loading bay 26, it being understood other IOL loading methods may be employed (including simply placing IOL 30 in loading bay 26 with a pair of forceps, for example). As explained in more detail in these copending applications, the retainer 40 and IOL 30 may be coupled and packaged together or coupled to and packaged with an injector device 12 such that the surgeon or nurse need not handle and/or manipulate the IOL directly when loading the IOL 30 into the device 10. It is also understood that the IOL configuration shown and described herein is for discussion purposes only, and that the present invention is not to be limited thereby. The invention may be easily adapted to IOLs of any configuration and type (e.g., IOLs with plate, open or closed loop haptics, anterior chamber IOLs, posterior chamber IOLs, accommodating IOLs (including single and double lens types), etc.).

Referring still to FIG. 1A, the plunger tip 22 is configured for engaging the IOL optic 31 at the periphery 31a thereof as the plunger 20 is advanced toward the tip opening 18a of the injector body 12. It is understood that other plunger tip designs may be used with the present invention as desired. It is furthermore preferred that the plunger shaft is rotationally fixed within lumen 14 to prevent unexpected rotation of the shaft (and thus the tip 22) with the lumen 14. The plunger shaft may be rotationally fixed by forming the proximal shaft length 20b and lumen 14 non-circular in cross-section or by including rotational fixing elements on the lumen inner wall and plunger shaft (e.g., longitudinal flange on the plunger having a sliding fit within a longitudinally extending groove provided on the lumen inner wall).

Figure 1B:
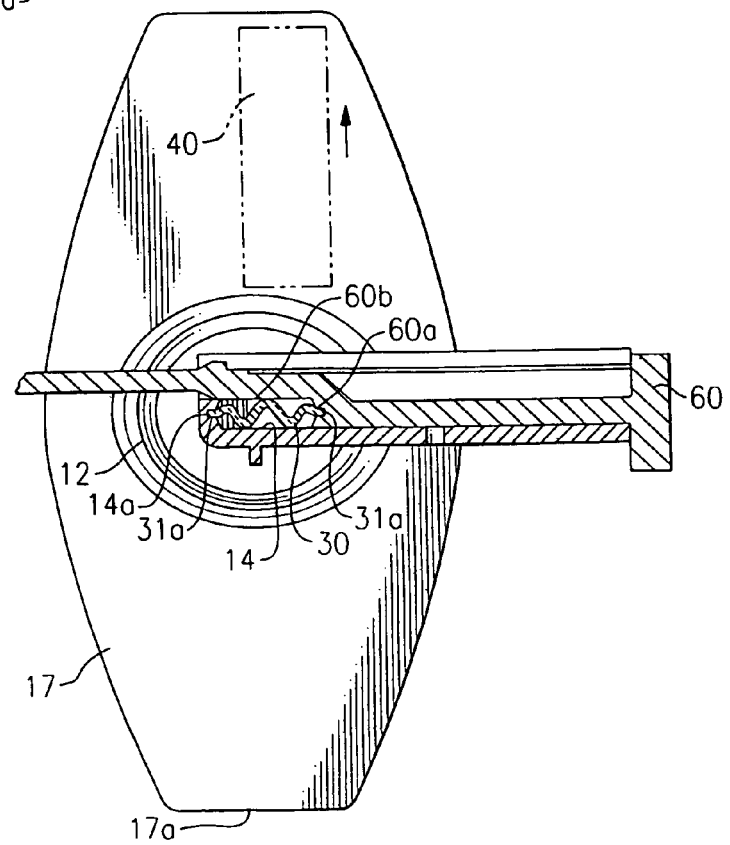
FIG. 1B is a cross-sectional view taken generally along the line 1B-1B in FIG. 1A showing the compressor drawer in the closed position and the IOL in the compressed condition.
Figure 2:
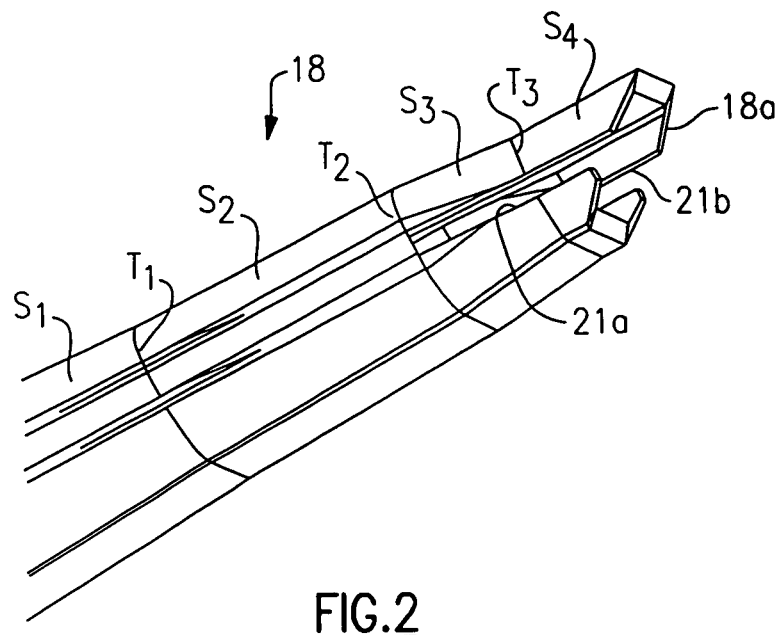
FIG. 2 is an enlarged, fragmented, perspective view of the inventive tip.
Figure 3:
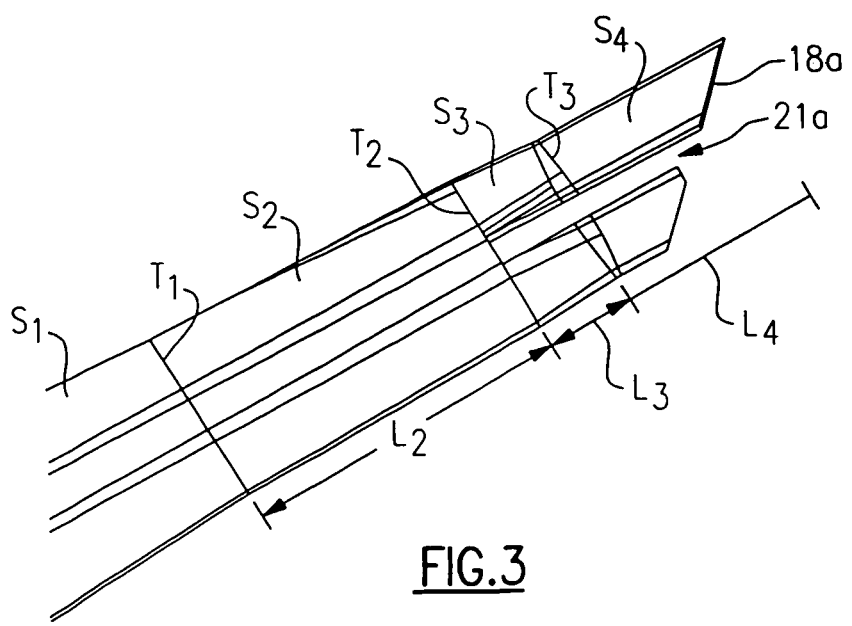
FIG. 3 is a side elevational view thereof.
Figure 4:
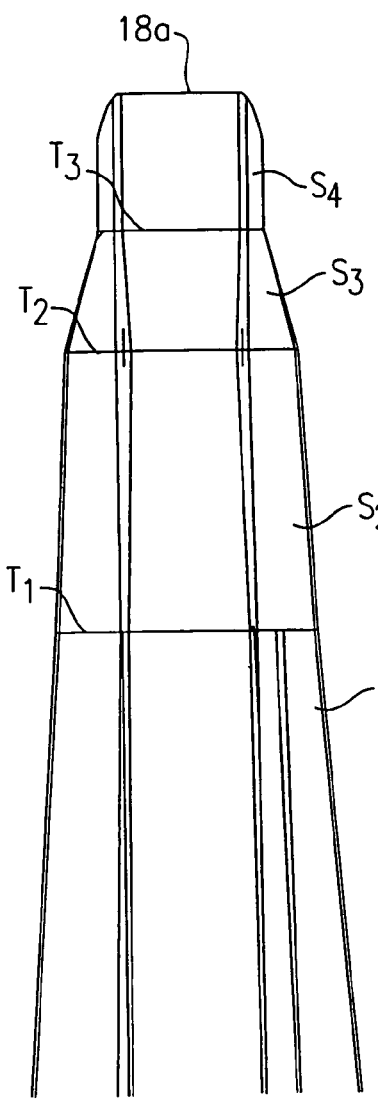
FIG. 4 is a top plan view thereof.
Figure 5:
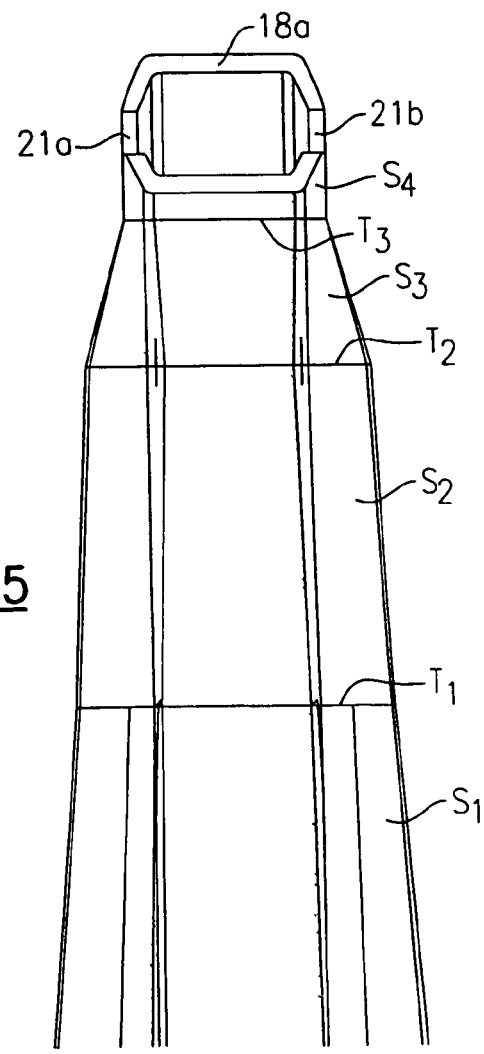
FIG. 5 is a bottom plan view thereof.

The injector includes means for compressing, rolling or otherwise forcing the IOL into a smaller cross-section for delivery through the injector. In the embodiment of FIG. 1A, the injector device includes a compressor drawer 60 which extends laterally of the IOL loading bay 26 of the injector body 12. The compressor drawer 60 is movable between fully open and fully closed positions and is initially in the open position to provide access to opening 26 for placement of the IOL therein. Referring to FIG. 1B, upon moving compressor drawer 60 to the fully closed position, the opposite edge of the optic periphery 31a becomes engaged in groove 60a of drawer 60. Thus, lumen 14 together with lumen groove 14a, drawer groove 60a, and drawer top wall 60b compresses and encases IOL optic 31 within lumen 14. The locating of the optic periphery 31a inside opposite grooves 14a and 60a ensures a planar delivery of the IOL 30 through lumen 14 and out tip 18. This manner of IOL planar delivery is described in more detail in commonly assigned U.S. Pat. No. 6,491,697.

Figure 6:
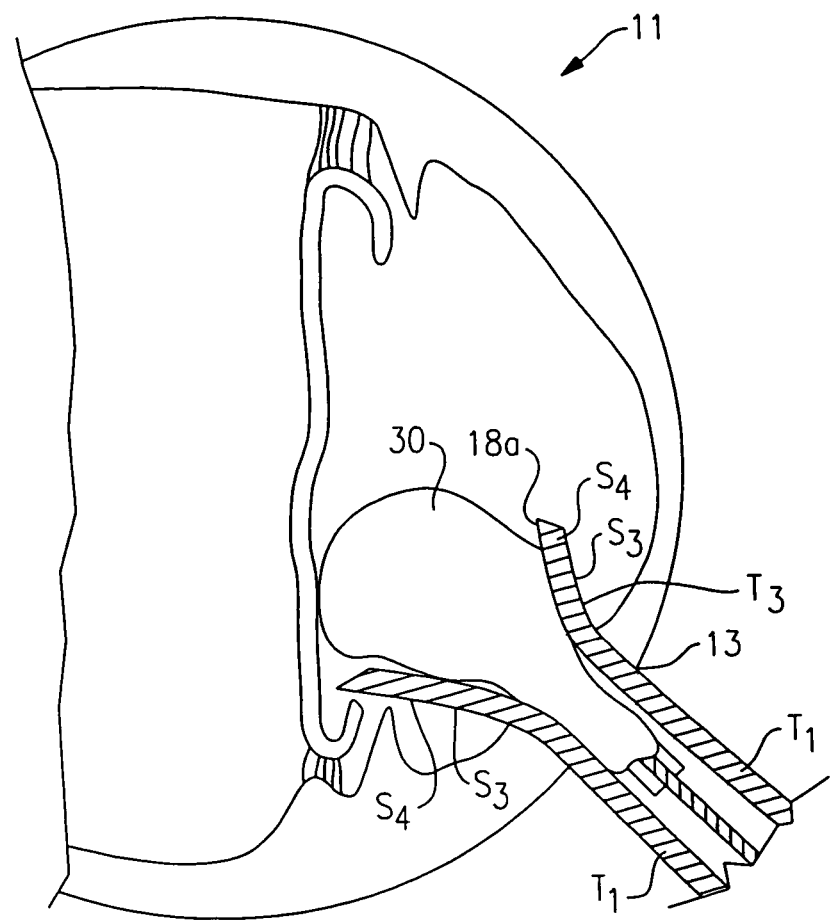
FIG. 6 is a schematic representation of an eye showing the anchoring effect of the tip within the eye as an IOL is being expressed from the tip.

Prior to closing compressor drawer 60 and compressing the IOL 30 inside the injector body, it may be desirable to apply viscoelastic to the area surrounding the IOL 30 to ease delivery of the IOL through the injector body. This is a common practice in the industry and the amount and location of viscoelastic application varies according to the instructions for use provided with the device as well as the desires of the surgeon. Once the viscoelastic has been applied as desired, the compressor drawer 60 is moved to the fully closed position whereupon the IOL optic 31 is compressed and ready for delivery through a small incision formed in an eye. The surgeon inserts the injector tip 18a into the incision cut into the eye (reference numeral 13 in FIG. 6) and begins advancing the plunger 20. As the plunger 20 is advanced, the plunger tip 22 engages the optic periphery 31a and pushes IOL 30 distally. Upon continued advancement of the plunger 20, the IOL 30 is pushed through the injector tip 18a and is finally expressed therefrom and into the eye 11 (FIG. 6).

For purposes of description, the injector tip may be considered as having four contiguous segments $S_1$-$S_4$ between the main body portion wherein the IOL is initially loaded into the device at an opening 26, and the open end of the tip 18a. It is understood that the tip may be separable from the main injector body or may be formed as a unitary construction therewith. The first, proximal segment $S_1$ is closest to the main body 12, the fourth, distal segment $S_4$ includes the open tip 18a, and the second and third segments $S_3$, $S_3$ extend sequentially therebetween. The first proximal segment $S_1$ tapers gradually inwardly for a first length $L_1$ (FIG. 1A.) to gradually further compress the IOL as it is being advanced by the plunger toward the open end of the tip 18a. The second segment $S_2$ preferably has a substantially constant diameter for a second length $L_2$ (FIGS. 2-5) which is preferably smaller than length $L_1$. The juncture of the first and second segments $S_1$, $S_2$ define a first transition point $T_1$ having an outer diameter of about 2.7 mm to about 3.1 mm, and more preferably about 2.8 mm. Since the second segment $S_2$ preferably remains constant in diameter, the surgeon may insert the device anywhere along second segment $S_2$ and not stretch the incision as would occur if this segment were tapered. Furthermore, the IOL is not compressed any further as it is passed through this segment by the plunger. The third segment $S_3$ tapers inwardly at a greater rate than the taper of segment $S_1$ for a length $L_3$ that is preferably smaller than $L_1$ or $L_2$. The fourth segment $S_4$ preferably has a continuous diameter extending for a length $L_4$ also preferably smaller than $L_1$ or $L_2$, terminating in a slanted end face defining the open end of the tip 18a. The juncture of the third and fourth segments $S_3$, $S_4$ define a third transition point $T_3$ having an outer diameter of about 2.0 mm to about 2.6 mm, and more preferably about 2.4 mm. Some surgeons will use the injector device by inserting the tip up to the first transition point $T_1$ which has an outer diameter not exceeding about 3.0 mm and more preferably about 2.8 mm. This means the incision in the eye need not be larger than about 3 mm. Current surgeon preference is to have an incision no larger than about 3 mm, and preferably sub 3 mm. Yet there are other surgeons that may prefer an even smaller incision size on the order of about 2.4 mm. For these surgeons, they may insert the tip up to only the third transition point $T_3$ as shown in FIG. 6 which, as stated above, has an outer diameter in the range of about 2.0 to 2.6 mm and more preferably about 2.4 mm.

At least one but preferably two slots 21a, 21b extend from the second transition point $T_2$ to the tip open end face. The slots reduce the hoop (radial) strength of the tip along the third and fourth segments $S_3$, $S_4$ for reasons explained below. The slots may colinearly extend from respective grooves 14a, 14b (14b not shown but is coextensive with drawer groove 60a seen in FIG. 1B) extending along the inside wall of the lumen through the tip wherein opposite sides of the IOL optic periphery 31a slide during passage of the IOL through the device and into the eye. Since the slots reduce the hoop strength of the tip along segments $S_3$, $S_4$, the inserted segment $S_4$ will spread outwardly under the force exerted by the compressed IOL as it travels through those segments as seen in FIG. 6. For surgeons who prefer to insert the tip only up to the third transition point $T_3$, the spreading action of this portion of the tip effectively "anchors" the inserted portion (segment $S_4$) of the tip in the eye until the IOL has completely exited the device. This anchoring effect is important in preventing the surgeon from losing control of the IOL insertion process, especially in those circumstances where the surgeon prefers to insert only up to the point of the third transition point $T_3$ to maintain a very small diameter incision (i.e., in the range of about 2.0 to 2.5 mm). To explain, with only a small length of the tip inserted through the incision (i.e., only up to point $T_3$), and without such anchoring of the tip within the eye, the force of the IOL exiting the tip may cause an inserter to decenter and/or kick back from the incision, possibly resulting in incorrect placement within the eye or the IOL expressing from the tip completely outside of the eye. The anchoring effect of the inventive tip thus ensures the tip will remain centered in the incision and in the eye until the IOL is completely expressed from the tip. Once the IOL is fully expressed from the tip into the eye, the resiliency of the tip causes the tip to return to its normal diameter (as seen in FIGS. 1-5) allowing easy withdrawal of the tip from the eye with no stretching of the incision.

The injector tip is thus dimensioned to allow the surgeon to choose an insertion depth between first, second or third transition points defined on the tip, with the first and second transition points being larger in diameter than the third transition point and all diameters being about or less than 3 mm. If the surgeon wishes to insert through an incision around or just below 3 mm, the surgeon may insert the device up to the first or second transition point $T_1$, $T_2$. If the surgeon instead wishes to insert through a very small incision size (e.g., about 2.4 mm), the surgeon will insert the tip only up to the third transition point $T_3$ and the insertion device will remain stable owing to the unique anchoring design thereof.

What is claimed is:

1. An injector for delivering a foldable IOL into an eye, comprising:
    an injector body having a tip comprising a first segment, a second segment and a third segment, the third segment extending to an open end of the injector body, the open end being adapted to permit the IOL to exit the injector into the eye,
    at least one slot extending from the open end through the second segment and the third segment, the third segment connected to the second segment at a transition point, the transition point characterized by a change in taper of an outer dimension of the tip.

2. The injector of claim 1, wherein the third segment has a constant outer diameter.

3. The injector of claim 1, wherein the open end has a slanted face.

4. The injector of claim 1, wherein the at least one slot comprises at least two slots.

5. The injector of claim 4, further comprising a lumen extending through the tip, and two lumen grooves extending along the lumen, each of the slots colinearly extending from a corresponding one of the lumen grooves.

6. The injector of claim 5, further comprising a compressor drawer extending from a loading bay of the injector body, the drawer movable between an open position and a closed position.

7. The injector of claim 6, wherein the compressor drawer comprises a drawer groove.

8. The injector of claim 7, wherein the drawer groove is aligned with one of the lumen grooves.

9. The injector of claim 2, wherein the constant outer diameter is about 2.0 to 2.5 mm.

10. The injector of claim 9, wherein the change in taper is a discrete change in taper.

11. The injector of claim 1, wherein the first segment is unslotted.

12. The injector of claim 1, wherein the first segment has a different taper than the second segment.

13. The injector of claim 12, wherein the second segment has a constant outer diameter.

14. The injector of claim 1, wherein the first segment is configured to compress a lens transported therethrough.

15. The injector of claim 1, wherein the second segment has a greater taper than the third segment.

16. The injector of claim 1, comprising a second transition point between the first and the second segments, an outer diameter at the second transition point being larger than an outer diameter at the transition point between the third segment and the second segment.

17. The injector of claim 16, wherein the second transition point characterized by a change in taper of an outer dimension of the tip.

18. The injector of claim 17, wherein the at least one slot does not extend through the first segment.

* * * * *